US005834245A

United States Patent [19]
Nakamura et al.

[11] Patent Number: 5,834,245
[45] Date of Patent: Nov. 10, 1998

[54] PRLTS PROTEINS AND DNA'S ENCODING THE SAME

[75] Inventors: Yusuke Nakamura, Kanagawa; Yoshiyuki Fujiwara, Tokyo, both of Japan

[73] Assignees: Cancer Institute; Eisai Co., Ltd., both of Tokyo, Japan

[21] Appl. No.: 506,864

[22] Filed: Jul. 25, 1995

[30] Foreign Application Priority Data

Jul. 29, 1994 [JP] Japan ..................................... 6-178131

[51] Int. Cl.⁶ ............................ C12N 15/12; C12N 15/63
[52] U.S. Cl. ...................... 435/69.3; 435/320.1; 435/325; 435/360; 435/361; 435/362; 435/365.1; 435/365; 435/367; 435/252.3; 435/252.33; 435/254.11; 536/23.5
[58] Field of Search .......................... 536/23.5; 435/69.3, 435/320.1, 325, 360, 361, 362, 365.1, 365, 367, 252.3, 252.33, 254.11

[56] References Cited

FOREIGN PATENT DOCUMENTS

84/03564   9/1984   WIPO .

OTHER PUBLICATIONS

Genes, Chromosomes & Cancer, vol. 10, 1 May 1994, pp. 7–14.
Nature, vol. 323, 18 Sep. 1986, pp. 226–232.
Mol. Cell. Biol., vol. 8, No. 8, Aug. 1988, pp. 3476–3486.
Oncogene, vol. 5, 1990, pp. 519–524.
S.H. Friend et al, Proc. Natl. Acad. Sci. USA, Dec. 1987, vol. 84, pp. 9059–9063.
D.P. Lane et al, Nature, 15 Mar. 1979, vol. 278, pp. 261–263.
K.W. Kinzler et al, Science, 9 Aug. 1991, vol. 253, pp. 661–665.
K.M. Call, et al, Cell, 9 Feb. 1990, vol. 60, pp. 509–520.
D. Malkin et al, Science, 30 Nov. 1990, vol. 250, pp. 1233–1238.
S. Srivastava et al, Nature, 20/27 Dec. 1990, vol. 348, pp. 747–749.
M.L. Brandi et al, Endocrine Reviews, Nov. 1987, vol. 8, No. 4, pp. 391–405.
E. Takahashi et al, Human Genetics, 15 Nov. 1989, vol. 86, pp. 14–16.
Y. Nakamura et al, Am. J. Hum. Genet., 1988, vol. 43, pp. 854–859.
A.J. Buckler, et al, Proc. Natl. Acad. Sci., May 1991, vol. 88, pp. 4005–4009.
A.M. Maxam et al, Proc. Natl. Acad. Sci., Feb. 1977, vol. 74, No. 2, pp. 560–564.
J. Messing et al, Nucleic Acids Research, 1981, vol. 9, No. 2, pp. 309–321.
A. Hinnen et al, Proc. Natl. Acad. Sci., Apr. 1978, vol. 75, No. 4, pp. 1929–1933.
C. Gorman et al, Science, 5 Aug. 1983, vol. 221, pp. 551–553.
A. Becker et al, Proc. Nat. Acad. Sci., Feb. 1975, vol. 72, No. 2, pp. 581–585.
C. Cepko et al, Cell, Jul. 1984, vol. 37, pp. 1053–1062.
T. Sato et al, Cancer Research, 15 Nov. 1990, vol. 50, pp. 7184–7189.
D. Wu et al, Genomics, 1989, vol. 4, pp. 560–569.
G. Ruano et al, Nucleic Acids Research, 1989, vol. 17, No. 20, pp. 8392–8393.
C.R. Newton et al, Nucleic Acids Research, 1989, vol. 17, No. 7, pp. 2503–2517.
M. Orita et al, Proc. Natl. Acad. Sci., Apr. 1989, vol. 86, pp. 2766–2770.
M. Orita et al., Genomics, 1989, vol. 5, pp. 874–879.
C. Larsson et al, Nature, 3 Mar. 1988, vol. 332, pp. 85–87.
Y. Nakamura et al, Am. J. Hum. Genet., 1989, vol. 44, pp. 751–755.
T. Tokino et al, Am. J. Hum. Genet., 1991, vol. 48, pp. 258–268.
A. Tanigami et al, Am. J. Hum. Genet., 1992, vol. 50, pp. 56–64.
T. Hori et al, Genomics, 1992, vol. 13, pp. 129–133.
Emi, M., et al., Cancer Res., vol. 52, pp. 5368–5372 (1992).
Ohata, H., et al., Genes Chromosomes & Cancer, vol. 7, pp. 85–88 (1993).
Emi, M., et al., Genes Chromosomes & Cancer, vol. 7, pp. 152–157 (1993).
Fujiwara, Y., et al., Cancer Res., vol. 53, pp. 1172–1174 (1993).
Bergerheim, U., et al., Genes Chromosomes & Cancer, vol. 3, pp. 215–220 (1991).
Knowles, M.A., et al, Oncogene, vol. 8, pp. 1357–1364 (1993).
FISH technique; Inazawa et al., Genomics, vol. 10, pp. 1075–1078 (1991).
PDGFR–b; Yarden, Y., et al., Nature, vol. 323, pp. 226–232 (1986).
flt; Shibuya, M., et al., Oncogene, vol. 5, pp. 519–524 (1990).
Orita, M., et al., Cell, vol. 60, pp. 509–520 (1990).
Winter, E., Perucho, M., et al., Proc. Natl. Acad. Sci. USA. vol. 82, pp. 7575–7579 (1985).
Myers, R.M., et al., Science, vol. 230, pp. 1242–1246 (1985).

(List continued on next page.)

*Primary Examiner*—Anthony C. Caputa
*Attorney, Agent, or Firm*—Flynn,Thiel, Boutell & Tanis, P.C.

[57]   ABSTRACT

A gene is provided which is present in the deletion region of a chromosome common in lung cancer, hepatocellular carcinoma and colorectal cancer and encodes a novel protein, a protein encoded by the gene (PRLTS protein), and a method of discriminating tumor cells. With respect to the human chromosome 8, a detailed gene map was prepared, the chromosome of each of lung cancer, hepatocellular carcinoma and colorectal cancer tissues was analyzed, and a gene encoding a novel protein was cloned to thereby determine the structure thereof. A gene analysis was conducted with the use of a DNA probe derived from the above gene, and consequently mutations in the gene were confirmed in the lung cancer, hepatocellular carcinoma and colorectal cancer tissues.

4 Claims, 5 Drawing Sheets

OTHER PUBLICATIONS

Koi et al., Jpn. J. Cancer Res., vol. 80, pp. 413–418 (1989).
Emi, M., et al., Genomics, vol. 15, pp. 530–534 (1993).
Inazawa et al., Jpn. J. Cancer Res., vol. 83, pp. 1248–1252 (1992).
Inazawa et al., Cytogenet, Cell Genet., vol. 65, pp. 130–135 (1994).

PRLTS PROTEINS AND DNA'S ENCODING THE SAME

BACKGROUND OF THE INVENTION

1. Field of the Invention

The present invention relates to PRLFS proteins, DNAs encoding the proteins and methods of discriminating tumor cells in which use is made of the DNAs. The present invention is usefully applied in the fields of medical science and pharmaceuticals.

2. Description of the Related Art

There has long been a conception that mutations in cellular proteins play an important role in carcinogenesis. The progress of genetic engineering achieved in recent years has made it possible to analyze the amplification of the DNA encoding a specified protein and gene mutations in tumor cells, thereby rapidly advancing cancer research.

The analysis and identification of genes (oncogenes) encoding proteins believed as participating in the malignant alteration of cells and the abnormal proliferation of tumor cells have been promoted, so that the identification of such genes number in the tens. On the other hand, counteracting genes (tumor suppressor genes) are highlighted in recent years. Tumor suppressor genes hitherto discovered include the Rb gene capable of suppressing retinoblastoma [Friend, S. H., et al., Proc. Natl. Acad. Sci. USA., 84, 9095 (1987)], the p53 gene capable of suppressing colorectal cancer [Lane, D. P., et al., Nature, 278, 261 (1979)], the APC gene capable of suppressing colorectal cancer [Kenneth, W. K., et al., Science, 253, 661 (1991)] and the WTI gene capable of suppressing Wilms' tumor [Call, K. M., et al., Cell, 60, 509 (1990)]. With respect to the p53 gene, cases are known in which germ-line mutations in the gene are inherited ["Li-Fraumeni syndrome" (Makin, D., et al., Science, 250, 1233 (1990); and Srivastava, S., et al., Nature, 348, 747 (1990))]. It is gradually becoming apparent that defects in not only a single gene but also in multiple genes participate in the progression of the malignant phenotype of cancer, and it is believed that there will be further discovered a large number of unidentified oncogenes and tumor suppressor genes. Their discovery and elucidation are anticipated by not only research and clinical experts but also people worldwide.

It is estimated that there are about 4500 genes on the human chromosome 8, and to now the presence of genes causative of genetic diseases such as Langer-Gideorn syndrome, Werner syndrome and pigmentous retinitis is suggested on this chromosome. The present inventors and other researchers reported [Emi, M., et al., Cancer Res., 52, 5368–5372 (1992)] that on the short arm of the human chromosome 8 there is a site frequently deleted in various tumors such as lung cancer [Ohata, H., et al., Genes Chromosomes & Cancer, 7, 85–88 (1993)], hepatocellular carcinoma [Emi, M., et al., Genes Chromosomes & Cancer, 7, 152–157 (1993)], colorectal cancer [Fujiwara, Y., et al., Cancer Res., 53, 1172–1174 (1993)], prostatic cancer [Bererheim, U., et al., Genes Chromosomes & Cancer, 3, 215–220 (1991)] and bladder cancer (Knowles, M. A., et al, Oncogene, 8, 1357–1364 (1993)] and that, hence, the presence of an important tumor suppressor gene capable of participating in various cancers is foreseen in the above deletion site.

Therefore, isolation of the causative gene present in the above site and identification of a protein corresponding thereto are now themes of great concern of not only worldwide doctors and researchers but also the general public, whose attainment is highly anticipated.

DISCLOSURE OF THE INVENTION

Summary of the Invention

An object of the present invention is to provide a novel protein related to tumors such as lung cancer, hepatocellular carcinoma, colorectal cancer and prostatic cancer, a gene encoding the same, and a method of discriminating tumor cells from normal cells with the use thereof.

The present inventors have further localized the region of the short arm of the human chromosome 8 which is commonly deleted in lung cancer, hepatocellular carcinoma and colorectal cancer.

More specifically, numerous cosmid clones having DNA fragments of the human chromosome 8 introduced thereinto have been prepared, and their positions on the chromosome has been determined in accordance with the fluorescent in situ hybridization technique [FISH technique; Inazawa et al., Genomics, 10, 1075–1078 (1991)]. From among the resultant markers, one having the property of having different restriction fragment lengths depending on the individual (RFLP: restriction fragment length polymorphism), i.e., an RFLP marker has been selected.

The RFLP marker has the feature that, by the use thereof, two homologous chromosomes inherited from the parents can be discriminated according to the difference in polymorphism [when, however, both exhibit the same polymorphic pattern, the discrimination cannot be made (not informative)]. Such a phenomenon that this difference in polymorphic pattern between the two homologous chromosomes (heterozygosity) is present in normal tissues and disappears in carcinoma tissues (LOH: loss of heterozygosity) means the deletion of the RFLP marker site in one of the homologous chromosomes. Further, generally, it is believed that the inactivation of tumor suppressor gene on both of the chromosomes which is attributed, for example, to a deletion in one of a pair of chromosomes and a mutation in the other leads to a malignant alteration and that a tumor suppressor gene is present in a region commonly deleted in numerous tumors.

The present inventors have investigated the LOH of the short arm of the chromosome 8 with respect to each of about 100 cases of human hepatocellular carcinoma, about 120 cases of colorectal cancer and about 50 cases of nonsmall cell lung cancer by the use of the obtained detailed physical chromosomal map and the RFLP marker. As a result, the minimal deletion region which is common in them has been identified.

Partial deletions in the short arm of the chromosome 8 in human hepatocellular carcinoma (HCC) and lung cancer (LC) are shown in FIG. 1. Each solid circle refers to the loss of heterozygosity (LOH), while each open circle to the retention thereof.

Partial deletions in the short arm of the chromosome 8 in colorectal cancer (CRC) are shown in FIG. 2. Each solid circle refers to the loss of heterozygosity (LOH), while each open circle to the retention thereof.

The designation of each cosmid clone used as a probe, the determined position thereof on the chromosome, and the LOH are collectively given in Table 1.

TABLE 1

| designation of probe | physical localization | enzyme | probe fragment (kb) | allele size (kb) | loss of heterozygosity (LOH) HCC (%) | CRC (%) | LC (%) |
|---|---|---|---|---|---|---|---|
| C18-1344 | 8p22 | MspI | Msp I 4.8 | 4.5 2.6/1.9 | 10/40 (25) | 25/71 (35) | 8/30 (27) |
| C18-2195 | 8p21.3–p22 | MspI | Tsq I 5.0 | 3.8 2.6 | 7/32 (22) | 15/35 (43) | 6/20 (30) |
| C18-2014 | 8p21.3–p22 | TaqI | Tsq I 3.9 | 3.9 2.2/1.7 | 2/6 (33) | 7/24 (29) | 71/7 (41) |
| cMSR-32 | 8p22 (MSR) | MspI | E-H 0.9 | 6.3/3.1 /2.9/2./ (4 alleles) | 10/54 (19) | 27/74 (36) | 16/38 (42) |
| cMSR-35 | 8p22 (MSR) | TaqI | Taq I 2.4 | 2.4 1.6 | 3/9 (33) | 16/33 (48) | 12/20 (60) |
| C18-2644 | 8p21.3–p22 | MspI | Msp I 2.9 | 5.5 2.9 | | 9/21 (43) | 15/22 (68) |
| | | TaqI | Msp I 2.4 | 4.0 0.6 | 2/6 (33) | | |
| C18-1051 | 8p22–p21.3 | MspI | Msp I 4.3 | 4.3 4.0 | 10/33 (30) | 19/42 (45) | 10/21 (48) |
| C18-487 | 8p22–p21.3 (D8S233) | MspI | MspI 1.2 | 1.2 1.0 | 5/14 (36) | 10/21 (48) | 3/7 (43) |
| C18-245 | 8p22–p21.3 (D8S335) | TaqI | MspI 7.0 | 4.8 4.2 and 3.0 1.8/1.2 | 4/18 (22) | 15/30 (50) | 12/27 (44) |
| C18-2439 | 8p21.3–p22 | TaqI | Msp I 2.8 | 2.3 1.6 | 9/40 (23) | 14/48 (29) | 7/22 (32) |
| C18-1312 | 8p21 | TaqI | Msp I 2.8 | 2.0 1.5 | 9/39 (23) | 22/49 (45) | 7/23 (30) |
| C18-190 | 8p1.3 (D8S334) | TaqI | Tsq I 3.5 | 4.8 3.5 | 8/37 (22) | 18/49 (37) | 8/19 (42) |
| C18-1013 | 8p21.3 | MspI | Msp I 2.7 | 3.5 2.7 | 16/54 (30) | 31/51 (61) | 5/24 (21) |
| Ct8-1308 | 8p21 | MspI | Msp I 4.6 | 4.6 3.5 | 7/25 (28) | 8/20 (40) | 4/17 (24) |

The above regions conform to each other, and two YAC (Y738 and Y812) clones covering the most localized common deletion region (8p21.3 to 8p22) have been isolated (see FIG. 3).

A cosmid contig covering the common deletion region has been constructed by subcloning the YAC DNA into cosmids.

DNA fragments capable of serving as exons have been taken through selection from the above cosmids according to an exon amplification technique. Subsequently, cDNA libraries have been screened with the use of the above DNA fragments as probes, thereby obtaining a plurality of cDNA clones derived from the genes present in the common deletion region. Whether or not a tumor-tissue-specific gene rearrangement is detected has been investigated with the use of these cDNA clones as probes according to the Southern blotting analysis. As a result, when one cDNA clone has be en used as a probe, a gene rearrangement apparent in one case of pulmonary nonsmall cell carcinoma has been recognized.

This clone has encoded a novel protein exhibiting a significant similarity to the N-terminal domain (extracellular domain) of each of platelet-derived growth factor receptor b [PDGFR-b; Yarden, Y., et al., Nature, 323, 226–232 (1986)] and fms-like tyrosine kinase [fit; Shibuya, M., et al., Oncogene, 5, 519–524 (1990)]. This protein has been designated PRLTS (PDGF receptor beta-like tumor suppressor) protein. Whether or not there are any mutations in human hepatocellular carcinoma, pulmonary nonsmall cell carcinoma and colorectal cancer with respect to the nucleic acid sequence of the coding region of this gene have been investigated. As a result, three cases of apparent mutations in the gene have been identified. Thus, it has become apparent that the defect or deficiency in this protein and the deletion or mutation in the DNA encoding the protein deeply participate in the progression of various tumors including hepatocellular carcinoma and pulmonary nonsmall cell carcinoma.

The present invention is of the utmost importance in that, through investigations of, for example, whether or not there is any defect or deficiency in this protein and whether or not there is any deletion or mutation in the DNA encoding the protein, it provides schemes and material for resolving difficult problems such as risk diagnosis, early detection, progress observation, determination of treatment plan and presumption of prognosis at least as regards hepatocellular carcinoma, pulmonary nonsmall cell carcinoma and colorectal cancer, so that this field of technology can be rapidly advanced.

Thus, the present invention relates to (1) a PRLTS protein having an amino acid sequence comprising the whole or a part of the amino acid sequence specified in sequence ID NO 1, (2) a DNA having a nucleic acid sequence comprising the whole or a part of the nucleic acid sequence specified in any of sequence ID NO 2, 3, 4, 5, 6, 7, 8 and 9, (3) a vector containing a DNA having a nucleic acid sequence comprising the whole or a part of the nucleic acid sequence specified in sequence ID NO 2, (4) a transformant having, introduced thereinto, the vector described in the above item (3), (5) a process for producing the PRLTS protein described in the above item (1) which comprises using the transformant described in the above item (4), (6) a DNA probe or primer (which may be a single stranded one) having a sequence comprising the whole or a part of the nucleic acid sequence specified in sequence ID NO 2, (7) an antiserum, a polyclonal antibody or a monoclonal antibody capable of combining with a PRLTS protein having the amino acid sequence specified in sequence ID NO 1, and (8) a method of discriminating tumor cells which comprises detecting the genomic mutation of a DNA encoding a PRLTS protein having an amino acid sequence comprising the whole or a part of the amino acid sequence specified in sequence ID NO 1.

The present invention comprehends proteins which are substantially equivalent to the above protein and which are obtained by addition, deletion, insertion or substitution of one or more constituent amino acids of the above protein, and DNAs which are substantially equivalent to the above DNA and which are obtained by addition, deletion, insertion or substitution of one or more constituent bases (nucleotides) of the above DNA.

The DNA having a nucleic acid sequence comprising the whole or a part of the nucleic acid sequence of the DNA according to the present invention, or comprising a sequence complementary to the whole or a part of the nucleic acid sequence of the DNA according to the present invention, can be utilized in gene analysis and diagnosis as the primer or probe. The term "part of the nucleic acid sequence" as used herein means a sequence of at least six continuous bases (nucleotides), preferably at least eight bases, and still more preferably 10 to 12 bases or 15 to 25 bases corresponding to (i.e., contained in or complementary to) the nucleic acid sequence of the DNA encoding the PRLTS protein. The primer or probe of the present invention, which is an oligonucleotide or polynucleotide, may also contain at least one base not corresponding to the nucleic acid sequence of the DNA encoding the PRLTS protein.

The whole or a part of the PRLTS protein can be used as an epitope in the preparation of antibodies and as agents for research and diagnosis using such antibodies. The term "epitope" as used herein refers to an artigenic determinant of a polypeptide. It is publicly known that a polypeptide composed of 6 amino acids combines with an antibody [see WO of PCT Patent Applications No. 8403564, published on Sep. 13, 1984 (Assignee: COMMONWEALTH SERUM LABS AND GEYSEN, H. M.)]. The term "part of the amino acid sequence" as used herein means a sequence of at least six continuous amino acids, preferably at least eight to ten amino acids, and still more preferably at least 11 to 20 amino acids corresponding to (i.e., contained in) the amino acid sequence of the PRLTS protein according to the present invention. The polypeptide having an amino acid sequence comprising a part of the amino acid sequence described above may also contain at least one amino acid not corresponding to the amino acid sequence of the PRLTS protein. Naturally, polypeptides each composed of at least 20 consecutive amino acids can also be used.

DETAILED DESCRIPTION OF THE INVENTION

The present invention will now be described in greater detail.

(1) Isolation of cDNA clone

Cosmid clones of the human chromosome 8 can be prepared in, for example, the following manner. From a human-mouse hybrid cell line containing a single human chromosome 8 in a mouse genomic background, a genomic DNA is extracted. Then, DNA fragments of the genomic DNA can be integrated into a vector, such as pWEX15, according to the method reported by Tokino et al. [Tokino et al., Am. J. Hum. Genet., 48, 258–268 (1991)]. Then, clones having an insert originating from the human chromosome can be screened therefrom by conducting colony hybridization with the use of a whole human DNA as the probe.

The thus-obtained large number of cosmid clones each containing a DNA originating from the human chromosome 8 are then subjected to the FISH technique. Thus, of the large number of cosmid clones can be localized throughout the chromosome, and a detailed physical chromosomal map can be prepared with the use of the cosmid clones as the marker. Further, RFLP markers can be isolated on the basis of the fragment length pattern of which has been prepared by the digestion of human DNA with several restriction enzymes [Nakamura et al., Am. J. Hum. Genet., 43, 854–859 (1988)]. With the use of the above map and RFLP markers, the DNA of a tumor tissue of a patient is examined in the LOH (loss of heterozygosity). Thus, the common deletion region on the chromosome in the tumor tissue can be localized into an extremely restricted region in the vicinity of from p21.3 to 22 of the human chromosome 8.

A cosmid contig of this localized common deletion region can be constructed by selecting a YAC clone having the genomic DNA of this region and subsequently preparing a cosmid library on the basis of the DNA of the YAC clone. Further, DNA fragments having sequences capable of serving as exons can be selected from restriction enzyme fragments of the cosmid clones according to the exon amplification technique [Buckler et al., Proc. Natl. Acad. Sci. USA., 88, 4005–4009 (1991)]. cDNAs of the genes present in the localized region in the vicinity of from p21.3 to 22 of the human chromosome 8 can be cloned by screening cDNA libraries with the use of the thus-obtained DNA fragments as probes. A clone having a sequence included in the tumor-tissue-specific gene rearrangement can be screened from the above cDNAs according to the Southern blotting analyses. The nucleic acid sequence of the cDNA can be determined according to the common procedure (Maniatis, J., et al., Molecular Cloning 2nd. ed., Cold Spring Harbor Laboratory Press, N.Y., 1989).

The cDNA clone thus-obtained can be confirmed to be the desired causative gene clone by searching for the presence of mutation and the frequency of mutation in cancer patients according to the SSCP method [Orita, M., et al., Genomics, 5, 874–879 (1984) and Orita, M., et al., Cell, 60, 509–520 (1990)] or the RNase protection method [Winter, E., Perucho, M., et al., Proc. Natl. Acad. Sci. USA. 82, 7575–7579 (1985) and Myers, R. M., et al., Science, 230, 1242-1246 (1985)] regarding the sequence thereof.

(2) Confirmation of the whole structure of the gene

It has been confirmed that the cDNA obtained by the above procedure has a novel DNA sequence specified in sequence ID NO 2, and it has been deduced that the amino acid sequence of a novel protein encoded thereby is as specified in sequence ID NO 1. Proteins each having an amino acid sequence comprising the whole or a part of the sequence specified in sequence ID NO 1 have been designated PRLTS proteins by the present inventors and will be referred to as the same hereinafter. Moreover, the nucleic acid sequence of the genomic DNA has been analyzed and compared with that of the cDNA, so that intron-exon combining sites have been confirmed and the structures of sequence ID NO's 3, 4, 5, 6, 7, 8 and 9 including introns and exons have been elucidated.

(3) Recombinant expression vectors and transformants thereof

The DNA encoding human PRLTS protein obtained by the above-mentioned procedure or a fragment thereof can be integrated into a suitable vector and introduced by transfection into a suitable host cell, thereby obtaining a transformant. This transformant can be cultured in a conventional manner. The human PRLTS protein can be produced in large quantity from the culture. More particularly, the DNA encoding the human PRLTS protein or a fragment thereof can be recombined with a vector suitable for expression thereof downstream of the promoter of the vector according to the customary procedure in which a restriction enzyme and a DNA ligase are employed, thereby obtaining a recombinant expression vector. Although plasmids pBR322 and pUC18 derived from *Escherichia coli*, plasmid pUB110 derived from *Bacillus subtilis*, plasmid pRB15 derived from yeast, bacteriophage vectors λgt10 and λgt11, and vector SV40 may be mentioned as examples of suitable vectors, the vectors are not particularly limited as long as they can be replicated and amplified in the host. With respect to the types of promoter and terminator as well, they are not particularly limited as long as they are adapted to the host for use in the expression of the DNA sequence encoding the human PRLTS protein and appropriate combinations can be effected depending on the host. The employed DNA is by no way limited as long as it encodes the human PRLTS protein. The employed DNA is not limited to those having the nucleic acid sequences specified in sequence ID NO 2, 3, 4, 5, 6, 7, 8 and 9. The DNAs may be those having a nucleic acid sequence resulting from intentional or nonintentional substitution, deletion, insertion and/or addition, conducted independently or in combination, of part of each of the nucleic acid sequences described above. The above DNA may be prepared by any nonlimited method, including biological and chemical methods. The thus-obtained recombinant expression vector is introduced into a host according to any of various methods such as the competent cell method [J. Mol. Biol., 53, 154 (1970)], the protoplast method [Proc. Natl. Acad. Sci. USA., 75, 1929 (1978)], the calcium phosphate method [Science, 221, 551 (1983)], the in vitro packaging method [Proc. Natl. Acad. Sci. USA., 72, 581 (1975)] and the virus vector method [Cell, 37, 1053 (1984)], thereby preparing a transformant. For example, *Escherichia coli*, *Bacillus subtilis*, yeast and animal cells can be used as the host. The resultant transformant is cultured in a medium suitable for the host. The culturing is generally effect ed at 20° to 45° C. and pH 5 to 8. According to necessity, ventilation and agitation are conducted. Separation of the PRLTS protein from the culture and purification thereof can be effected by a suitable combination of conventional separation and purification means. Examples of the above conventional means include salting out, solvent precipitation, dialysis, gel filtration, electrophoresis, ion exchange chromatography, affinity chromatography and reversed phase high-performance liquid chromatography.

(4) Preparation of antibody

The antibody can be prepared by the use of the whole or a part of the PRLIS protein as the antigen according to the customary procedure. For example, a polyclonal antibody is prepared by inoculating an animal such as a mouse, a guinea-pig and a rabbit by subcutaneous, intramuscular, intraperitoneal or intravenous injection of the antigen more than one time to thereby satisfactorily immunize the animal, sampling blood specimen from the animal and separating sera from the blood specimen. Also, commercially available adjuvants can be used.

The monoclonal antibody can be prepared, for example, by conducting cell fusion of the splenocyte of a mouse immunized with the PRLTS protein and a commercially available mouse myeloma cell to thereby obtain a hybridoma and recovering from the hybridoma culture supernatant or from the ascites of a mouse in which the hybridoma has been injected.

The PRLTS protein for use as the antigen does not necessarily have to possess the entire amino acid structure. It may be a peptide having a partial structure thereof, a mutant thereof, a derivative thereof or a peptide resulting from fusion with another peptide. These may be prepared by any of customary methods including biological and chemical methods. The resultant antibody accomplishes identification and quantitative determination of the PRLTS protein in human biospecimens and can be used as diagnostic agents for cancer, carcinoma or tumors. The immunological determination of the PRLTS protein may be achieved in accordance with publicly known methods, for example, the fluorescent antibody method, the passive agglutination reaction method and the enzyme antibody method.

(5) Gene analysis with respect to human tumor tissue

For example, human blood, body fluid and secretory fluid as well as human normal tissues and various human tumor tissues can be used as the biospecimens subjected to gene analysis. The extraction and preparation of DNA is performed by, for example, the method of Sato et al. [Sato, T., et al., Cancer Res., 50, 7184 (1990)].

The presence or absence of mutation in the gene can be analyzed with the use of restriction enzyme fragments of the DNA encoding the human PRLTS protein according to the present invention as the probe or with the use of an oligonucleotide synthesized by appropriately selecting a nucleic acid sequence located in a suitable position from the above DNA as the primer.

Further, any defects such as insertion and deletion in the gene of each specimen can be detected by the above analyses.

The selected nucleic acid sequence site can be any of the gene's exons, gene's introns and combining sites thereof. Further, artificially modified nucleic acid sequences can naturally be employed, by which the corresponding gene mutations can be detected.

The above analysis can be conducted by, for example, a method in which amplification of a partial sequence is conducted with the use of primers having two types of sequences selected according to the PCR method and the nucleic acid sequence of an amplification product is directly analyzed or a method in which this amplification product is integrated into a plasmid in the same manner as described above, a host cell is transformed by the plasmid and cultured, and the nucleic acid sequence of the obtained clone is analyzed. Alternatively, the presence or absence of a specified mutation in the above gene of each specimen can be directly detected by the use of the ligase chain reaction method [Wu et al., Genomics, 4, 560–569 (1989)] and further the mutant-sequence-specific PCR method [Ruano and Kidd, Nucleic Acid Research, 17, 8392 (1989) and C. R. Newton et al., Nucleic Acid Research, 17, 2503–2517 (1989)].

Similarly, a point mutation can be detected with the use of a probe including a selected DNA sequence or RNA sequence derived therefrom according to the SSCP method and the RNase-protection method. Moreover, any mutation in the gene of each specimen in the Southern hybridization method and any abnormality in the quantity of expression attained by the gene of each specimen in the Northern hybridization method can be detected with the use of such a probe.

The *Escherichia coli* 68cDNA into which the plasmid containing the DNA encoding the PRLTS protein was introduced was deposited with the National Institute of Bioscience and Human-Technology, Agency of Industrial Science and Technology, Ministry of International Trade and Industry under the accession number FERM BP-4658 on Apr. 27, 1994.

Expectations are entertained of the use of the human PRLTS protein and the DNA containing the whole or a part of the DNA encoding this protein according to the present invention as agents for investigating, testing/diagnosing and treating tumors.

EXAMPLES

Figure 1:
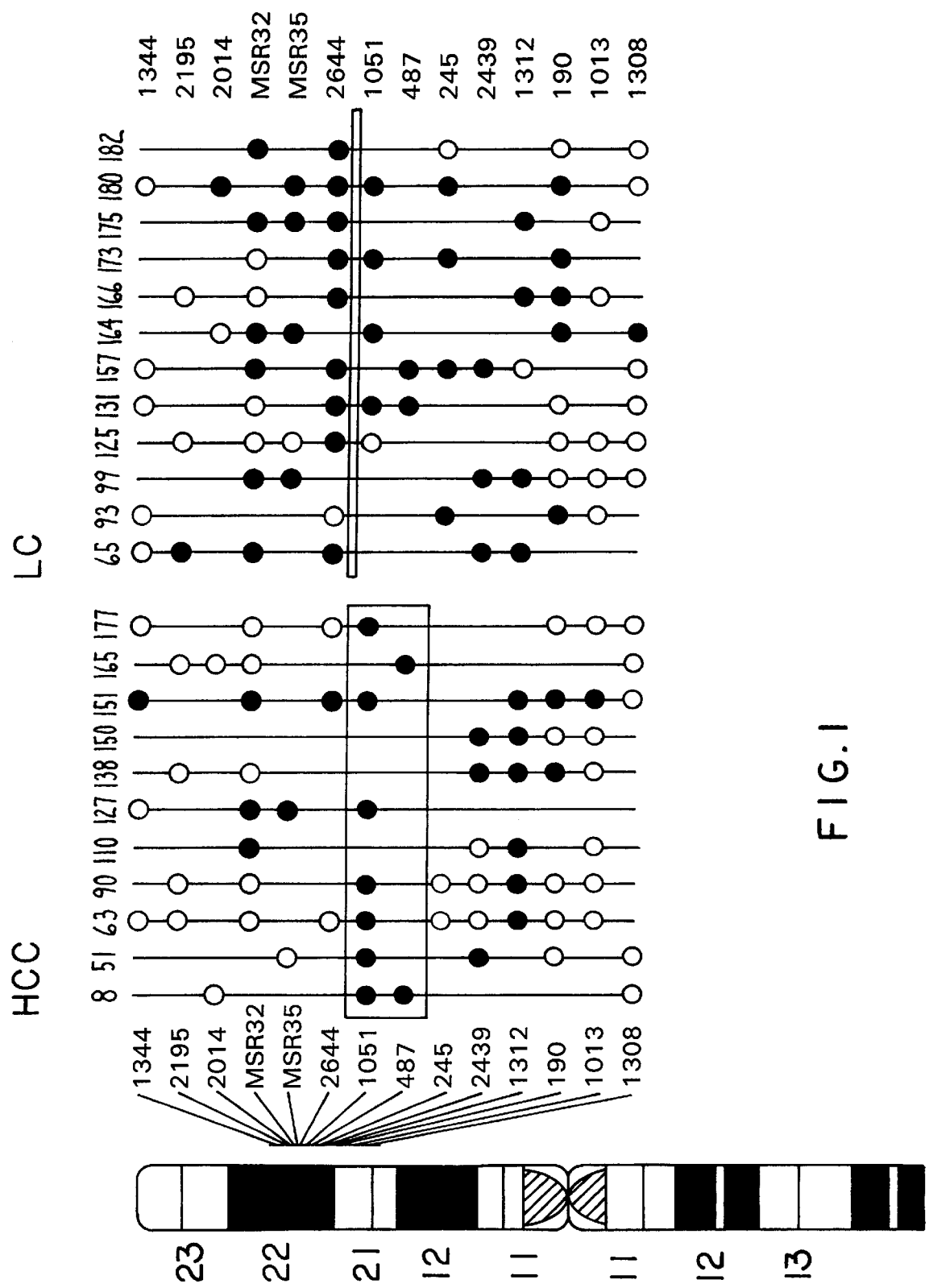
FIG. 1 shows partial deletions in the short arm of the human chromosome 8 in human hepatocellular carcinoma (HCC) and lung cancer (LC), in which each solid circle refers to the loss of heterozygosity (LOH), while each open circle to the retention thereof, and each rectangular frame to the common deletion region, and in which each clone is indicated by its number only.

The present invention will now be described in greater detail and more specifically with reference to the following Examples, which by no means limit the invention.

(Example 1)
Isolation of cosmid clones specific to the human chromosome 8 and preparation of chromosome map Cosmid clones specific to the human chromosome 8 were isolated in accordance with the method of Tokino et al. [Tokino et al., Am. J. Hum. Genet., 48, 258–268 (1991)]. Specifically, the genomic DNA of human-mouse hybrid cell line A9neo8/t containing a single human chromosome 8 in a mouse genomic background [Koi et al., Jpn. J. Cancer Res., 80, 413–418 (1989)] was appropriately digested with restriction enzyme Sau3AI, and the terminals of the resultant fragments were treated by partial filling-in in which dATP and dGTP were employed. Then, fragments having a size of 35 to 42 kb were fractionated from the treated fragments and inserted into cosmid vectors pWEX15 which had been subjected to digestion with restriction enzyme XhoI and similar treatment by partial filling-in in which dCTP and dTTP were employed. Cosmid clones specific to the human chromosome 8 were isolated by screening clones containing human DNA fragments from the obtained cosmid clones in accordance with the colony hybridization method in which $^{32}$P-labeled human genomic DNA was used as the probe.

The positions on the chromosome where the above DNA fragments of cosmid clones were to be hybridized thereto were determined in accordance with the FISH method [Inazawa et al., Genomics, 10, 1075–1078 (1991)].

With respect to the cosmid clones whose positions on the chromosome were determined (cosmid markers), the detectability of RFLP was tested in accordance with the known method [Nakamura et al., Am, J. Hum. Genet., 43, 854–859 (1988)]. The restriction enzyme for use was selected from MspI, TaqI, BglII, PstI, PvuII, RsaI and EcoRI.

(Example 2)
Determination of the order of cosmid marker sites on the short arm of the human chromosome 8

For further limiting the region (8p21 to 8p23) on the short arm of the human chromosome 8 which would be commonly deleted in hepatocellular carcinoma, colorectal cancer and pulmonary nonsmall cell carcinoma and which was discovered by the present inventors [Emi, M., et al., Cancer Res., 52, 5368–5372 (1992)], the order of 14 polymorphic cosmid markers (RFLP markers) present within the above region which were obtained in Example 1 was determined (see Table 1). Of them, the order of four sites (CI8-190, CI8-245, CI8-487 and MSR-32) had already been determined by the genetic linkage analysis effected by the present inventors [Emi, M., et al., Genomics, 15, 530–534 (1993)], and the genetic distance between CI8-190 and MSR-32 sites was estimated to be 10 cM. With the use of individual cosmid markers including these four markers in combination, the multicolor FISH method [Inazawa et al., Jpn. J. Cancer Res., 20, 1248–1252 (1992) and Inazawa et al., Cytogenet. Cell Genet., 65, 130–135 (1994)] was repeatedly followed, thereby analyzing the relative positional relationship of the above markers. As a result, the order of the above 14 RFLP markers (denoted only by the number with omission of "CI8-") was determined as centromere - 1308 - 1013 - 190 - (1312, 2439) - (245, 487) - 1051 - (2644, MSR35, MSR32) - 2014 - 2195 - 1344 - telomere, although, with respect to the parenthesized markers, relative position divisions could not be attained by this method.

(Example 3)
Localization of the region of the short arm of the human chromosome 8 commonly deleted in hepatocellular carcinoma, pulmonary nonsmall cell carcinoma and colorectal cancer Tumor tissues were obtained from operative materials consisting of 102 cases of hepatocellular carcinoma, 53 cases of pulmonary nonsmall cell carcinoma and 123 cases of colorectal cancer. The corresponding normal tissues or peripheral blood samples were obtained from the individual patients. DNAs were extracted from these tissues and blood samples in accordance with the known method [Sato, T., et al. Cancer Res., 50, 7184–7189 (1990)]. Each of the DNAs was digested with a suitable restriction enzyme, followed by electrophoresis on 1.0% agarose gel, and Southern-transferred with 0.1N NaOH/0.1M NaCl by means of a nylon membrane [Sato, T., et al. Cancer Res., 50, 7184–7189 (1990)].

On the resultant membranes, Southern hybridization was conducted with the use of 14 RFLP markers whose order was determined in Example 2 as the probe [Sato, T., et al. Cancer Res., 50, 7184–7189 (1990)], thereby testing the LOH (loss of heterozygosity) (see Table 1).

In hepatocellular carcinoma, the heterozygosity could be discriminated (informative) by at least one marker in 93 cases, of which in 34 cases (37%) the LOH was detected by at least one marker. In pulmonary nonsmall cell carcinoma, 56 cases were informative with at least one marker, of which in 26 cases (46%) the LOH was detected by at least one marker. In colorectal cancer, 115 cases were informative with at least one marker, of which in 64 cases (54%) the LOH was detected by at least one marker.

Cases in which the presence of a partial deletion on the short arm of the human chromosome 8 (8p) could positively be judged from the above results, i.e., not only could the heterozygosity be discriminated (informative) with at least two markers but also the presence of a deletion portion (LOH detected) and a retention portion (LOH not detected) was demonstrated were collected and analyzed.

Figure 2:
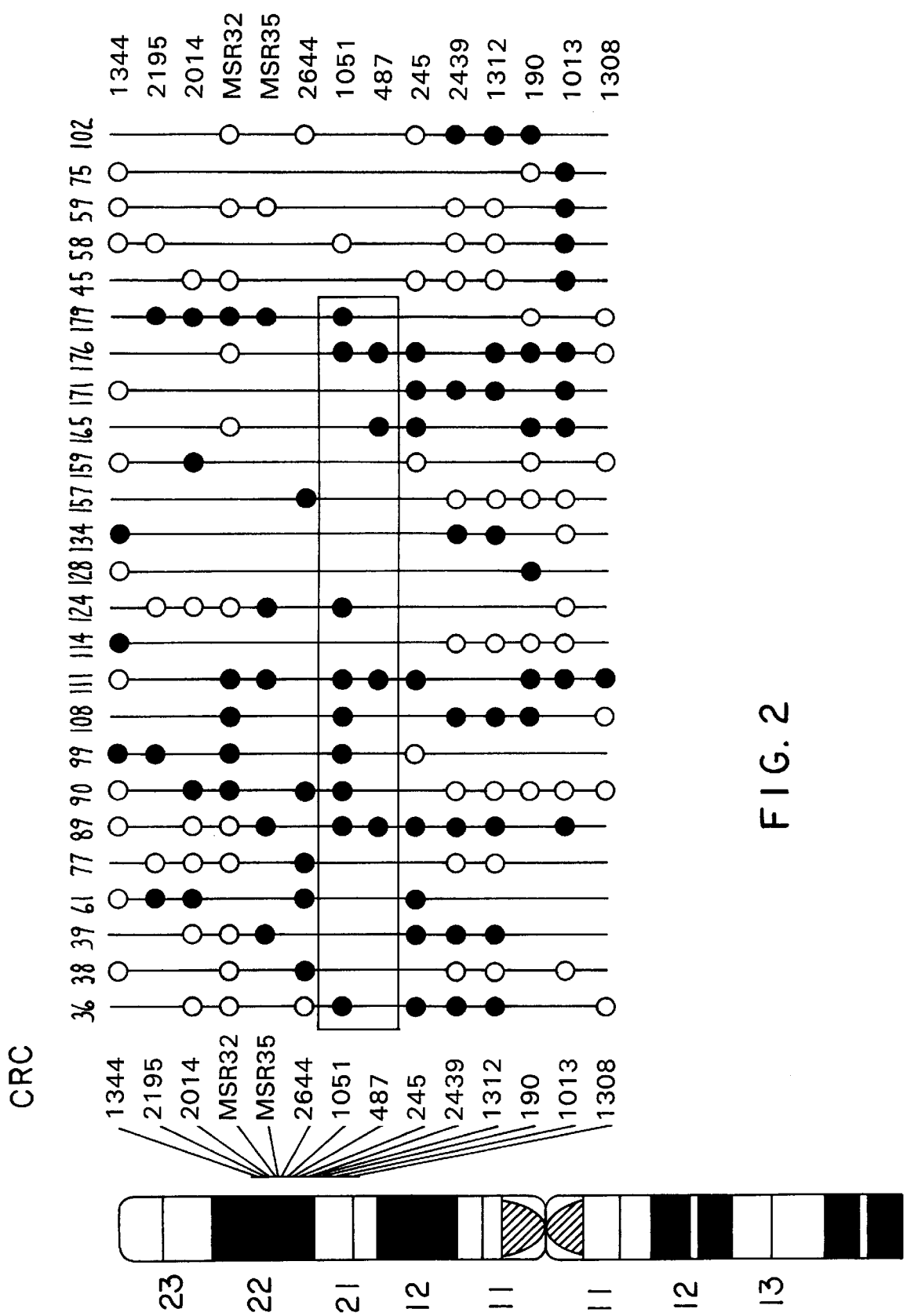
FIG. 2 shows partial deletions in the short arm of the human chromosome 8 in colorectal cancer (CRC), in which each solid circle refers to the loss of heterozygosity (LOH), while each open circle to the retention thereof, and the rectangular frame to the common deletion region, and in which each clone is indicated by its number only.

As a result, the common deletion region was localized between two markers CI8-245 and CI8-2644 in 11 cases of hepatocellular carcinoma (HCC) (see FIG. 1). Similarly, the common deletion region was localized between two markers CI8-1051 and CI8-2644 in 12 cases of pulmonary nonsmall cell carcinoma (LC) (see FIG. 1). Further, the common deletion region was localized between two markers CI8-245 and CI8-2644 in 25 cases of colorectal cancer (CRC) (see FIG. 2). The deletion region was common in these three tissue carcinomas (cancers) and localized in an especially narrow zone in pulmonary nonsmall cell carcinoma.

(Example 4)
Preparation of physical map by pulsed field gel electrophoresis (PFGE)

With respect to the common deletion region localized in Example 3, a physical map was prepared by PFGE analysis in which use was made of 12 DNA markers of the above region. Of these, eight DNA markers were polymorphic cosmid clones employed in the examination of LOH. As for the other four nonpolymorphic markers (CI8-1195, C18-2429, CI8-2003 and CI8-1372), their positions relative to CI8-1312 and cMSR-32 were determined in accordance with the multicolor FISH method.

Figure 4:
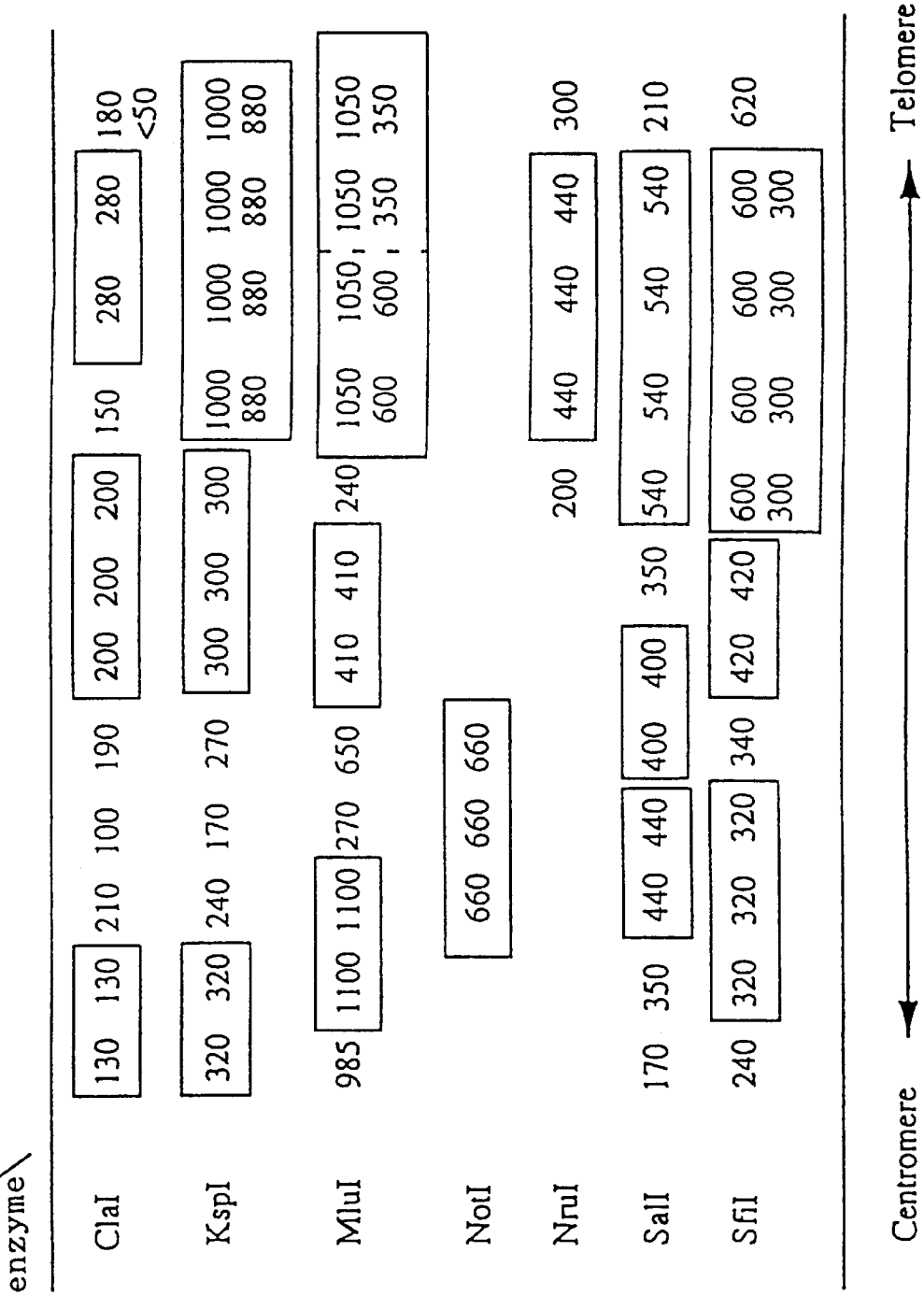
FIG. 4 shows the size of the restriction enzyme fragment identified by the genomic Southern blotting analyses, with the use of each DNA marker positioned around the localized common deletion region as the probe, in which the size is expressed in kb and each clone is indicated by its number only.

The genomic DNA was digested with seven types of restriction enzymes having rare breakage points, the thus-obtained fragments were subjected to PFGE, and a Southern blotting analysis was conducted with the use of each DNA marker as the probe. The size of the genomic DNA fragment identified by each of 12 DNA markers was summarized in FIG. 4.

No gap was recognized on this PFGE map, and the order of all the markers except cMSR-32 and CI8-2429 became apparent. The size of the most narrowly localized common deletion region (between CI8-1051 and CI8-2644) recognized in pulmonary nonsmall cell carcinoma was estimated to be about 600 kb.

(Example 5)
Preparation of the cosmid contig of the common deletion region

Figure 3:
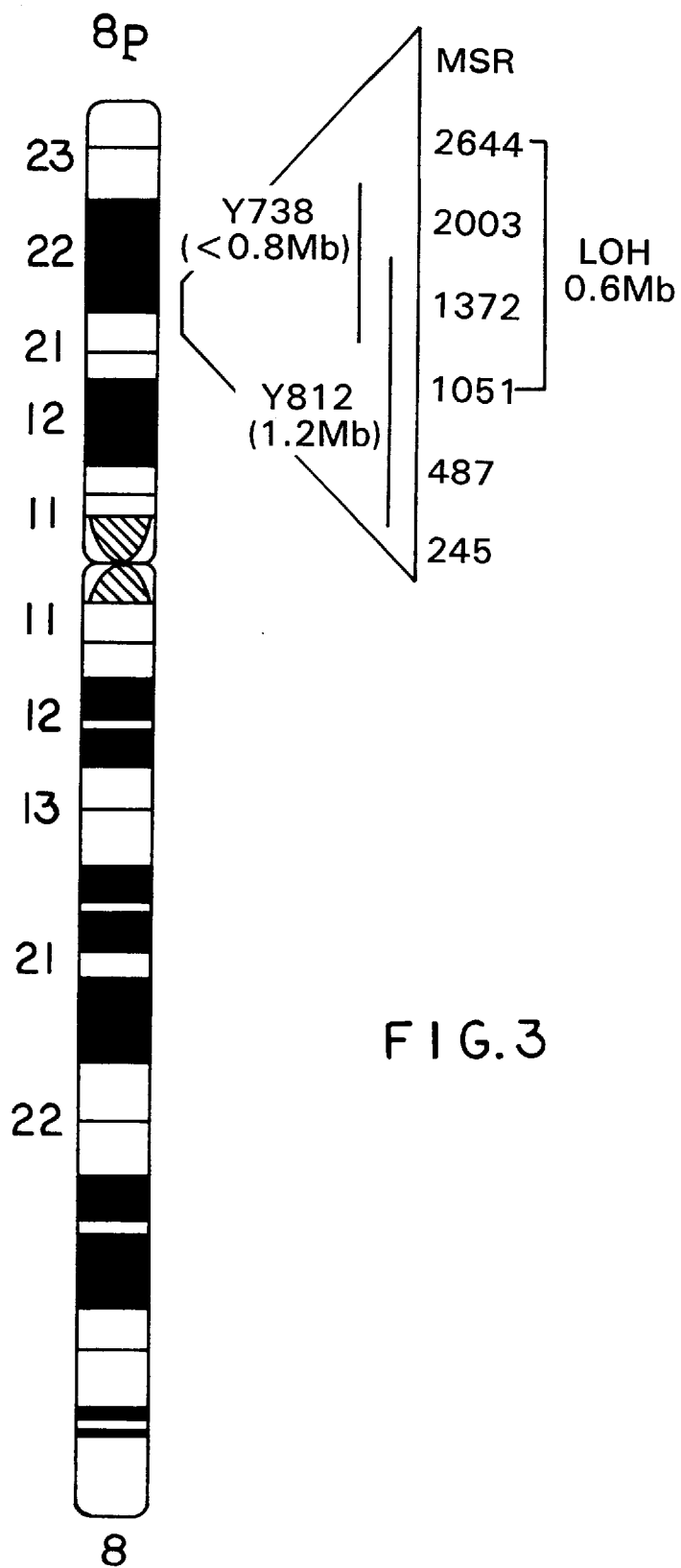
FIG. 3 shows the markers positioned in the common deletion region of the short arm of the human chromosome 8 and the positions of two YAC clones present in the region, in which each marker is indicated by the clone number only.

In order to isolate the genes present in this 600 kb region, the present inventors isolated two YAC clones, i.e., Y812 and Y738, each containing a genomic region ranging from cosmid marker CI8-487 to cosmid marker CI8-2003 (see FIG. 3). A cosmid Library was prepared from the DNAs of the above two YAC clones, and 74 clones having human DNAs were obtained. A cosmid contig map of these 74 cosmid clones was constructed in accordance with the Southern hybridization method.

(Example 6)
Isolation of genes from the common deletion region 34 cosmid clones covering the whole of the common deletion region were selected from the cosmid contig obtained in Example 5, and sequences capable of serving as exons were searched in accordance with the exon amplification method [Buckler et al., Proc. Natl. Acad. Sci. USA., 88, 4005-4009 (1991)]. As a result, 54 exon-like DNA fragments were obtained. cDNA libraries derived from a fetal lung and a fetal brain were each screened with the use of the above DNA fragments as probes. Thus, six mutually different cDNA clones were obtained.

(Example 7)
Detection of the gene rearrangement in tumor tissue

Figure 5:
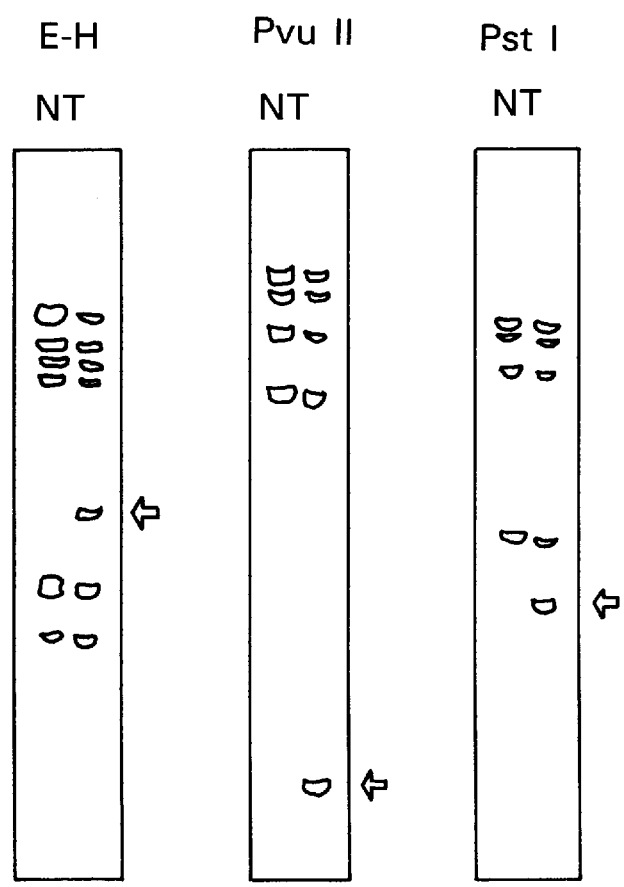
FIG. 5 shows Southern blotting detections of a gene rearrangement in lung cancer, in which N and T represent the DNAs of normal and tumor tissues, respectively.

The six types of cDNA clones were individually used as the probe to investigate whether any tumor-tissue-specific gene rearrangement would be detected. In particular, Southern blotting analysis was conducted with the use of the DNAs of the above cDNA clones as probes for fragments obtained by digestion of the DNAs of tumor tissues and normal tissues corresponding thereto with restriction enzyme(s) (EcoRI and HindIII, PvuII or PstI) to thereby detect any major abnormality in structural genes such as deletion, duplication, amplification and translocation occurring in tumor cells, namely, any gene rearrangement. A panel of DNAs in 295 cases consisting of 102 cases of hepatocellular carcinoma, 70 cases of pulmonary nonsmall cell carcinoma and 123 cases of colorectal cancer was investigated. As a result, when one cDNA clone was used as the probe, a gene rearrangement was detected in one case of pulmonary nonsmall cell carcinoma (see FIG. 5). Comparison in Southern blotting patterns of DNAs between the tumor tissue and the normal tissue showed the occurrence of this gene reconstitution in a tumor-tissue-specific manner.

It was confirmed that this clone was derived from the above common deletion region because it contained a sequence derived from cosmid cCI8-3068 whose position was in the middle between cCI8-1051 and cCI-2644 as found by the multicolor FISH. In this tumor, it was apparent that "two hit" somatic mutation occurred at the site including the above cDNA because the LOH was recognized with respect to both outside marker s cCI8-245 (D8S335) and cMSR-32 (MSR).

(Example 8)
Structure of cDNA

This cDNA clone was isolated from t he fetal lung cDNA library, and it was confirmed that this cDNA clone consisted of 1502 bp and had a novel DNA sequence including a 61 bp 5'-noncoding region, 1128 bp coding region and 313 bp 3'-noncoding region (see Sequence ID NO 2). This cDNA sequence contained an open reading frame which encoded a novel protein composed of 375 amino acids (PRLTS protein, see Sequence ID NO 1).

(Example 9)
Determination of the structure of genomic DNA

The presence of seven exons was confirmed by comparing the sequence of the genomic DNA of the cosmid clone with that of the cDNA obtained in Example 8 with respect to the sequence of the genomic DNA around exons. The exon-containing genomic DNA sequences are set forth in Sequence ID NO's 3, 4, 5, 6, 7, 8 and 9, in which the amino acid number corresponds to that of Sequence ID NO 1 to thereby represent the position number in the PRLTS protein.

(Example 10)
Detection of the gene mutation in tumor tissue

Single-strand conformation polymorphism (SSCP) analysis [Orita, M., et al., Genomics, 5, 874–879 (1984) and Orita, M., et al., Cell, 60, 509–520 (1990)] was conducted on the DNAs of 48 cases of hepatocellular carcinoma, 31 cases of pulmonary nonsmall cell carcinoma and 28 cases of colorectal cancer, thereby testing mutations in the genes. The SSCP analysis was conducted by amplifying the individual exons with the use of PCR primers having sequences (Sequence ID NO's 10 and 11, Sequence ID NO's 12 and 13, Sequence ID NO's 14 and 15, Sequence ID NO's 16 and 17, Sequence ID NO's 18 and 19, and Sequence ID NO's 20 and 21) designed from the sequence of the genomic DNA obtained in Example 9. The nucleic acid sequences of Sequence ID's NO 10 to 21 were designed from the sequences of Sequence ID's NO 3 to 9. There are the following relationships:

Sequence ID NO 10=Sequence ID NO 4, Nos. 3–24,
Sequence ID NO 11=Sequence ID NO 4, Nos. 281–300 antisense,
Sequence ID NO 12=Sequence ID NO 5, Nos. 49–71,
Sequence ID NO 13=Sequence ID NO 5, Nos. 393–415 antisense,
Sequence ID NO 14=Sequence ID NO 6, Nos. 5–24,
Sequence ID NO 15=Sequence ID NO 6, Nos. 207–231 antisense,
Sequence ID NO 16=Sequence ID NO 7, Nos. 34–53,
sequence ID NO 17=Sequence ID NO 7, Nos. 372–393 antisense,
Sequence ID NO 18=Sequence ID NO 8, Nos. 5–24,
Sequence ID NO 19=Sequence ID NO 8, Nos. 191–211 antisense,
Sequence ID NO 20=Sequence ID NO 9, Nos. 21–41, and
Sequence ID NO 21=Sequence ID NO 9, Nos. 263–285 antisense.

PCR products which had changes recognized in electrophoresis patterns as a result of the SSCP analysis were cloned and their nucleic acid sequences were determined. Consequently, point mutations accompanied by amino acid substitution were found in one case of colorectal cancer (CRC) and one case of hepatocellular carcinoma (HCC) and a mutation accompanied by 2-base deletion in one case of hepatocellular carcinoma (HCC) (see Table 2). By comparison of the nucleic acid sequence of the tumor tissue with that of the corresponding normal tissue, it was confirmed that these mutations were present only in tumor tissues.

TABLE 2

| tumor | codon | mutation | LOH |
|-------|-------|----------|-----|
| CRC20 | 23 | CAC (His) to TAC (Tyr) | + |
| HCC74 | 302 | GCG (Val) to GTG (Ala) | + |
| HCC107 | 175 | CTTTG to CTG | + |

In one case of colorectal cancer, CRC 20, a point mutation occurred from C to T, so that codon 23 changed from histidine to tyrosine. In this case, it was demonstrated that no normal C-containing sequence was detected in the nucleic acid sequence of the tumor DNA and that allelic deletion occurred. In hepatocellular carcinoma HCC 74, a point mutation occurred from C to T, so that codon 302 changed from valine to alanine. In another case of hepatocellular carcinoma, HCC 107, a frame shift occurred because of the mutation brought about by deletion of two bases at codon 175, so that a stop codon was formed downstream. In these cases as well, allelic deletion occurred in the tumor cell.

What we claim is:

1. An isolated DNA fragment which encodes a PRLTS protein having the amino acid sequence specified in sequence ID NO 1.

2. A vector containing an isolated DNA fragment which encodes a PRLTS protein having the amino acid sequence specified in sequence ID NO 1.

3. An isolated transformed host cell comprising a vector containing an isolated DNA fragment which encodes a PRLTS protein having the amino acid sequence specified in sequence ID NO 1.

4. A process for producing a PRLTS protein having the amino acid sequence specified in sequence ID NO 1, which comprises culturing an isolated transformed host cell comprising a vector containing an isolated DNA fragment which encodes the PRLTS protein, and recovering the PRLTS protein.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 375
        ( B ) TYPE: amino acid
        ( C ) STRANDEDNESS:
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( A ) LIBRARY: human fetal lung cDNA library ( x i ) SEQUENCE DESCRIPTION:SEQ ID NO: 1:

```
Met Lys Val Trp Leu Leu Leu Gly Leu Leu Leu Val His Glu Ala Leu
 1               5                  10                  15

Glu Asp Val Thr Gly Gln His Leu Pro Lys Asn Lys Arg Pro Lys Glu
                20                  25                  30

Pro Gly Glu Asn Arg Ile Lys Pro Thr Asn Lys Lys Val Lys Pro Lys
            35                  40                  45

Ile Pro Lys Met Lys Asp Arg Asp Ser Ala Asn Ser Ala Pro Lys Thr
        50                  55                  60

Gln Ser Ile Met Met Gln Val Leu Asp Lys Gly Arg Phe Gln Lys Pro
65                  70                  75                  80
```

| | | | | | | | | | | | | | | |
|---|---|---|---|---|---|---|---|---|---|---|---|---|---|---|
|Ala|Ala|Thr|Leu|Ser<br>85|Leu|Leu|Ala|Gly|Gln<br>90|Thr|Val|Glu|Leu|Arg<br>95|Cys|
|Lys|Gly|Ser|Arg<br>100|Ile|Gly|Trp|Ser|Pro<br>105|Ala|Tyr|Leu|Asp<br>110|Thr|Phe|
|Lys|Asp|Ser<br>115|Arg|Leu|Ser|Val|Lys<br>120|Gln|Asn|Glu|Arg|Tyr<br>125|Gly|Gln|Leu|
|Thr|Leu<br>130|Val|Asn|Ser|Thr|Ser<br>135|Ala|Asp|Thr|Gly|Glu<br>140|Phe|Ser|Cys|Trp|
|Val<br>145|Gln|Leu|Cys|Ser|Gly<br>150|Tyr|Ile|Cys|Arg|Lys<br>155|Asp|Glu|Ala|Lys|Thr<br>160|
|Gly|Ser|Thr|Tyr|Ile<br>165|Phe|Phe|Thr|Glu|Lys<br>170|Gly|Glu|Leu|Phe|Val<br>175|Pro|
|Ser|Pro|Ser|Tyr<br>180|Phe|Asp|Val|Val|Tyr<br>185|Leu|Asn|Pro|Asp|Arg<br>190|Gln|Ala|
|Val|Val|Pro<br>195|Cys|Arg|Val|Thr|Val<br>200|Leu|Ser|Ala|Lys|Val<br>205|Thr|Leu|His|
|Arg|Glu<br>210|Phe|Pro|Ala|Lys|Glu<br>215|Ile|Pro|Ala|Asn|Gly<br>220|Thr|Asp|Ile|Val|
|Tyr<br>225|Asp|Met|Lys|Arg|Gly<br>230|Phe|Val|Tyr|Leu|Gln<br>235|Pro|His|Ser|Glu|His<br>240|
|Gln|Gly|Val|Val|Tyr<br>245|Cys|Arg|Ala|Glu|Gly<br>250|Gly|Arg|Ser|Gln<br>255|Ile|
|Ser|Val|Lys|Tyr<br>260|Gln|Leu|Leu|Tyr|Val<br>265|Ala|Val|Pro|Ser|Gly<br>270|Pro|Pro|
|Ser|Thr|Thr<br>275|Ile|Leu|Ala|Ser|Ser<br>280|Asn|Lys|Val|Lys|Ser<br>285|Gly|Asp|Asp|
|Ile|Ser<br>290|Val|Leu|Cys|Thr|Val<br>295|Leu|Gly|Glu|Pro|Asp<br>300|Val|Glu|Val|Glu|
|Phe<br>305|Thr|Trp|Ile|Phe|Pro<br>310|Gly|Gln|Lys|Asp|Glu<br>315|Arg|Pro|Val|Thr|Ile<br>320|
|Gln|Asp|Thr|Trp|Arg<br>325|Leu|Ile|His|Arg|Gly<br>330|Leu|Gly|His|Thr|Thr<br>335|Arg|
|Ile|Ser|Gln|Ser<br>340|Val|Ile|Thr|Val|Glu<br>345|Asp|Phe|Glu|Thr|Ile<br>350|Asp|Ala|
|Gly|Tyr|Tyr<br>355|Ile|Cys|Thr|Ala|Gln<br>360|Asn|Leu|Gln|Gly|Gln<br>365|Thr|Thr|Val|
|Ala|Thr<br>370|Thr|Val|Glu|Phe|Ser<br>375|

( 2 ) INFORMATION FOR SEQ ID NO: 2:

( i ) SEQUENCE CHARACTERISTICS:
        ( A ) LENGTH: 1502
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: human fetal lung cDNA library ( i x ) FEATURE:
        ( A ) NAME/KEY: CDS
        ( B ) LOCATION: 62..1189
        ( C ) IDENTIFICATION METHOD: experimental examination ( x i ) SEQUENCE DESCRIPTION: SEQ ID NO: 2:

```
CCTGCGTCCC CGCCCCGCNC AGCCGCCGCG CTCCTGCNCT CCGAGGTCCG AGGTTCCCGA                                              60

G ATG AAG GTC TGG CTG CTG CTT GGT CTT CTG CTG GTG CAC GAA GCG                                                106
  Met Lys Val Trp Leu Leu Leu Gly Leu Leu Leu Val His Glu Ala
  1               5                   10                  15

CTG GAG GAT GTT ACT GGC CAA CAC CTT CCC AAG AAC AAG CGT CCA AAA                                              154
Leu Glu Asp Val Thr Gly Gln His Leu Pro Lys Asn Lys Arg Pro Lys
                20                  25                  30

GAA CCA GGA GAG AAT AGA ATC AAA CCT ACC AAC AAG AAG GTG AAG CCC                                              202
Glu Pro Gly Glu Asn Arg Ile Lys Pro Thr Asn Lys Lys Val Lys Pro
            35                  40                  45

AAA ATT CCT AAA ATG AAG GAC AGG GAC TCA GCC AAT TCA GCA CCA AAG                                              250
Lys Ile Pro Lys Met Lys Asp Arg Asp Ser Ala Asn Ser Ala Pro Lys
        50                  55                  60

ACG CAG TCT ATC ATG ATG CAA GTG CTG GAT AAA GGT CGC TTC CAG AAA                                              298
Thr Gln Ser Ile Met Met Gln Val Leu Asp Lys Gly Arg Phe Gln Lys
    65                  70                  75

CCC GCC GCT ACC CTG AGT CTG CTG GCG GGG CAA ACT GTA GAG CTT CGA                                              346
Pro Ala Ala Thr Leu Ser Leu Leu Ala Gly Gln Thr Val Glu Leu Arg
80                  85                  90                  95

TGT AAA GGG AGT AGA ATT GGG TGG AGC TAC CCT GCG TAT CTG GAC ACC                                              394
Cys Lys Gly Ser Arg Ile Gly Trp Ser Tyr Pro Ala Tyr Leu Asp Thr
                100                 105                 110

TTT AAG GAT TCT CGC CTC AGC GTC AAG CAG AAT GAG CGC TAC GGC CAG                                              442
Phe Lys Asp Ser Arg Leu Ser Val Lys Gln Asn Glu Arg Tyr Gly Gln
            115                 120                 125

TTG ACT CTG GTC AAC TCC ACC TCG GCA GAC ACA GGT GAA TTC AGC TGC                                              490
Leu Thr Leu Val Asn Ser Thr Ser Ala Asp Thr Gly Glu Phe Ser Cys
        130                 135                 140

TGG GTG CAG CTC TGC AGC GGC TAC ATC TGC AGG AAG GAC GAG GCC AAA                                              538
Trp Val Gln Leu Cys Ser Gly Tyr Ile Cys Arg Lys Asp Glu Ala Lys
    145                 150                 155

ACG GGC TCC ACC TAC ATC TTT TTT ACA GAG AAA GGA GAA CTC TTT GTA                                              586
Thr Gly Ser Thr Tyr Ile Phe Phe Thr Glu Lys Gly Glu Leu Phe Val
160                 165                 170                 175

CCT TCT CCC AGC TAC TTC GAT GTT GTC TAC TTG AAC CCG GAC AGA CAG                                              634
Pro Ser Pro Ser Tyr Phe Asp Val Val Tyr Leu Asn Pro Asp Arg Gln
                180                 185                 190

GCT GTG GTT CCT TGT CGG GTG ACC GTG CTG TCG GCC AAA GTC ACG CTC                                              682
Ala Val Val Pro Cys Arg Val Thr Val Leu Ser Ala Lys Val Thr Leu
            195                 200                 205

CAC AGG GAA TTC CCA GCC AAG GAG ATC CCA GCC AAT GGA ACG GAC ATT                                              730
His Arg Glu Phe Pro Ala Lys Glu Ile Pro Ala Asn Gly Thr Asp Ile
        210                 215                 220

GTT TAT GAC ATG AAG CGG GGC TTT GTG TAT CTG CAA CCT CAT TCC GAG                                              778
Val Tyr Asp Met Lys Arg Gly Phe Val Tyr Leu Gln Pro His Ser Glu
    225                 230                 235

CAC CAG GGT GTG GTT TAC TGC AGG GCG GAG GCC GGG GGC AGA TCT CAG                                              826
His Gln Gly Val Val Tyr Cys Arg Ala Glu Ala Gly Gly Arg Ser Gln
240                 245                 250                 255

ATC TCC GTC AAG TAC CAG CTG CTC TAC GTG GCG GTT CCC AGT GGC CCT                                              874
Ile Ser Val Lys Tyr Gln Leu Leu Tyr Val Ala Val Pro Ser Gly Pro
                260                 265                 270

CCC TCA ACA ACC ATC TTG GCT TCT TCA AAC AAA GTG AAA AGT GGG GAC                                              922
Pro Ser Thr Thr Ile Leu Ala Ser Ser Asn Lys Val Lys Ser Gly Asp
            275                 280                 285

GAC ATC AGT GTG CTC TGC ACT GTC CTG GGG GAG CCC GAT GTG GAG GTG                                              970
Asp Ile Ser Val Leu Cys Thr Val Leu Gly Glu Pro Asp Val Glu Val
        290                 295                 300
```

| | | | | | | | | | | | | | | | |
|---|---|---|---|---|---|---|---|---|---|---|---|---|---|---|---|
| GAG | TTC | ACC | TGG | ATC | TTC | CCA | GGG | CAG | AAG | GAT | GAA | AGG | CCT | GTG | ACG | 1018 |
| Glu | Phe | Thr | Trp | Ile | Phe | Pro | Gly | Gln | Lys | Asp | Glu | Arg | Pro | Val | Thr | |
| | 305 | | | | 310 | | | | | 315 | | | | | | |
| ATC | CAA | GAC | ACT | TGG | AGG | TTG | ATC | CAC | AGA | GGA | CTG | GGA | CAC | ACC | ACG | 1066 |
| Ile | Gln | Asp | Thr | Trp | Arg | Leu | Ile | His | Arg | Gly | Leu | Gly | His | Thr | Thr | |
| 320 | | | | | 325 | | | | | 330 | | | | | 335 | |
| AGA | ATC | TCC | CAG | AGT | GTC | ATT | ACA | GTG | GAA | GAC | TTC | GAG | ACG | ATT | GAT | 1114 |
| Arg | Ile | Ser | Gln | Ser | Val | Ile | Thr | Val | Glu | Asp | Phe | Glu | Thr | Ile | Asp | |
| | | | | 340 | | | | | 345 | | | | | 350 | | |
| GCA | GGA | TAT | TAC | ATT | TGC | ACT | GCT | CAG | AAT | CTT | CAA | GGA | CAG | ACC | ACA | 1162 |
| Ala | Gly | Tyr | Tyr | Ile | Cys | Thr | Ala | Gln | Asn | Leu | Gln | Gly | Gln | Thr | Thr | |
| | | | 355 | | | | | 360 | | | | | 365 | | | |
| GTA | GCT | ACC | ACT | GTT | GAG | TTT | TCC | TGACTTGGAA | | AAGGAAATGT | | AATGAACTTA | | | | 1216 |
| Val | Ala | Thr | Thr | Val | Glu | Phe | Ser | | | | | | | | | |
| | | 370 | | | | | 375 | | | | | | | | | |

| | | | | |
|---|---|---|---|---|
| TGGAAAGCCC | ATTTGTGTAC | ACAGTCAGCT | TTGGGGTTCC | TTTTATTAGT | GCTTTGCCAG | 1276 |
| AGGCTGATGT | CAAGCACCAC | ACCCCAACCC | CAGCGTCTCG | TGAGTCCGAC | CCAGACATCC | 1336 |
| AAACTAAAAG | GAAGTCATCC | AGTCTATTCA | CAGAAGTGTT | AACTTTCTA | ACAGAAGCA | 1396 |
| TGATTTTGAT | TGCTTACCTA | CATACGTGTT | CCTAGTTTTT | ATACATGTGT | AAACAATTTT | 1456 |
| ATATAATCAA | TCATTTCTAT | TAAATGAGCA | CGTTTTTGTA | AAAAAT | | 1502 |

( 2 ) INFORMATION FOR SEQ ID NO: 3:

( i ) SEQUENCE CHARACTERISTICS:
        ( A ) LENGTH: 281
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 1
        ( B ) LOCATION: 99..150
        ( C ) IDENTIFICATION METHOD: experimental examination ( x i ) SEQUENCE DESCRIPTION: SEQ ID NO: 3:

| | | | | | |
|---|---|---|---|---|---|
| AAATTCCCCA | ACTTTTTCCC | CCAAACCTTG | TTCCTCCTGA | AGAAACCGAA | TCCTCCCGCT | 60 |
| TCGGCGTCCC | AGGAGCCCGC | CCCTCGCCCG | CCGCCTCCCC | TGCGTCCCCG | CCCCGCNCAG | 120 |
| CCGCCGCGCT | CCTGCNCTCC | GAGGTCCGAG | GTTCCCGAGA | TNAAGGTCTG | GCTGCTGCTT | 180 |
| GGTCTTCTGC | TGGTGCNCCA | AGCGATGGAG | GATGGTGAGT | GACTCTGGGC | GCGGGGCCAC | 240 |
| CTAGCTTGGT | GCCCTGACTT | TAGCCGGGAC | CCGAAGTTTT | T | | 281 |

( 2 ) INFORMATION FOR SEQ ID NO: 4:

( i ) SEQUENCE CHARACTERISTICS:
        ( A ) LENGTH: 323
        ( B ) TYPE: nucleic acid
        ( C ) STRANDEDNESS: doubld
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
    ( A ) NAME/KEY: exon 2
    ( B ) LOCATION: 128..191
    ( C ) IDENTIFICATION METHOD: experimental examination ( x i ) SEQUENCE DESCRIPTION: SEQ ID NO: 4:

```
AAACCTTGTT  CCTCCTGAAG  AAACCGAATC  CTCCCGCTTC  GGCGTCCCAG  GAGCCCGCCC        60

CTCGCCCGCC  GCCTCCCCTG  CGTCCCCGCC  CCGCGCAGCC  GCCGGCTCCT  GCGCTCCGAG       120

GTCCGAGGTT  CCCGAG ATG  AAG GTC TGG CTG CTG CTT GGT CTT CTG CTG GTG         172
                   Met  Lys Val Trp Leu Leu Leu Gly Leu Leu Leu Val
                    1              5                      10

CAC GAA GCG CTG GAG GAT G GTGAGTGACT CTGGGCGCGG GGCCACCTAG                   221
His Glu Ala Leu Glu Asp Val
            15

CTTGTGCCCT  GACTTTAGCC  GGGACCCGAA  GCCCCGCCG  CCCTCCTGCC  AGCTCTTGGT        281

CTAACGTTCG  GCCCTCGGTG  GCTCAGCCCC  CGCNCCACTG  CC                          323
```

( 2 ) INFORMATION FOR SEQ ID NO: 5:

( i ) SEQUENCE CHARACTERISTICS:
        ( A ) LENGTH: 486
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 3
        ( B ) LOCATION: 74..371
        ( C ) IDENTIFICATION METHOD: experimental examination ( x i ) SEQUENCE DESCRIPTION: SEQ ID NO: 5:

```
AAAAAGTTAT  TGGCCTCAAA  TATTCCAAAA  ATGTCATTAC  TACAGNGNAT  TTCTCTCTCC        60

TTACGTTTTG  CAG TT ACT  GGC CAA CAC CTT CCC AAG AAC AAG CGT CCA AAA         111
               Val Thr  Gly Gln His Leu Pro Lys Asn Lys Arg Pro Lys
                    20                  25                      30

GAA CCA GGA GAG AAT AGA ATC AAA CCT ACC AAC AAG AAG GTG AAG CCC             159
Glu Pro Gly Glu Asn Arg Ile Lys Pro Thr Asn Lys Lys Val Lys Pro
                 35                  40                  45

AAA ATT CCT AAA ATG AAG GAC AGG GAC TCA GCC AAT TCA GCA CCA AAG             207
Lys Ile Pro Lys Met Lys Asp Arg Asp Ser Ala Asn Ser Ala Pro Lys
             50                  55                  60

ACG CAG TCT ATC ATG ATG CAA GTG CTG GAT AAA GGT CGC TTC CAG AAA             255
Thr Gln Ser Ile Met Met Gln Val Leu Asp Lys Gly Arg Phe Gln Lys
         65                  70                  75

CCC GCC GCT ACC CTG AGT CTG CTG GCG GGG CAA ACT GTA GAG CTT CGA             303
Pro Ala Ala Thr Leu Ser Leu Leu Ala Gly Gln Thr Val Glu Leu Arg
 80                  85                  90                  95

TGT AAA GGG AGT AGA ATT GGG TGG AGC TAC CCT GCG TAT CTG GAC ACC             351
Cys Lys Gly Ser Arg Ile Gly Trp Ser Tyr Pro Ala Tyr Leu Asp Thr
                100                 105                 110

TTT AAG GAT TCT CGC CTC AG GTAANCATTT TTTTTTAAAN CTGTGTAGGG                  401
Phe Lys Asp Ser Arg Leu Ser
            115
```

```
TTGAGGATTT   GTAATAGTTC   AAAATTCCTT   CTTAACTATT   ATTACACATT   GTTTCTGACA         461

TGTCCCATTT   TCCCCTAATA   GATCA                                                     486
```

( 2 ) INFORMATION FOR SEQ ID NO: 6:

( i ) SEQUENCE CHARACTERISTICS:
        ( A ) LENGTH: 231
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 4
        ( B ) LOCATION: 53..204
        ( C ) IDENTIFICATION METHOD: experimental examination ( x i ) SEQUENCE DESCRIPTION: SEQ ID NO: 6:

```
GGGCCCCAGC   CAGGTCTGAT   TTGCTTTGAG   TTCATGTGTC   TNTTATTCCT   NG  C   GTC          56
                                                                 Ser Val

AAG  CAG  AAT  GAG  CGC  TAC  GGC  CAG  TTG  ACT  CTG  GTC  AAC  TCC  ACC  TCG      104
Lys  Gln  Asn  Glu  Arg  Tyr  Gly  Gln  Leu  Thr  Leu  Val  Asn  Ser  Thr  Ser
120                      125                     130                     135

GCA  GAC  ACA  GGT  GAA  TTC  AGC  TGC  TGG  GTG  CAG  CTC  TGC  AGC  GGC  TAC      152
Ala  Asp  Thr  Gly  Glu  Phe  Ser  Cys  Trp  Val  Gln  Leu  Cys  Ser  Gly  Tyr
                         140                     145                     150

ATC  TGC  AGG  AAG  GAC  GAG  GCC  AAA  ACG  GGC  TCC  ACC  TAC  ATC  TTT  TTT      200
Ile  Cys  Arg  Lys  Asp  Glu  Ala  Lys  Thr  Gly  Ser  Thr  Tyr  Ile  Phe  Phe
               155                     160                     165

ACA  G   GTAAAATACT  TGGTGCATTA  ATGGAAC                                             231
Thr  Glu
```

( 2 ) INFORMATION FOR SEQ ID NO: 7:

( i ) SEQUENCE CHARACTERISTICS:
        ( A ) LENGTH: 423
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 5
        ( B ) LOCATION: 61..354
        ( C ) IDENTIFICATION METHOD: experimental examination ( x i ) SEQUENCE DESCRIPTION: SEQ ID NO: 7:

```
GNGTGCTNTN   ACTTTGCGTC   TCCGGAGTGN   ANAAGCCTGT   GCTCTTCCTT   CCCTTNGCAG           60

AG  AAA  GGA  GAA  CTC  TTT  GTA  CCT  TCT  CCC  AGC  TAC  TTC  GAT  GTT  GTC       107
Glu Lys  Gly  Glu  Leu  Phe  Val  Pro  Ser  Pro  Ser  Tyr  Phe  Asp  Val  Val
    170                      175                     180

TAC  TTG  AAC  CCG  GAC  AGA  CAG  GCT  GTG  GTT  CCT  TGT  CGG  GTG  ACC  GTG      155
Tyr  Leu  Asn  Pro  Asp  Arg  Gln  Ala  Val  Val  Pro  Cys  Arg  Val  Thr  Val
185                      190                     195                     200
```

```
CTG  TCG  GCC  AAA  GTC  ACG  CTC  CAC  AGG  GAA  TTC  CCA  GCC  AAG  GAG  ATC        203
Leu  Ser  Ala  Lys  Val  Thr  Leu  His  Arg  Glu  Phe  Pro  Ala  Lys  Glu  Ile
               205                     210                    215

CCA  GCC  AAT  GGA  ACG  GAC  ATT  GTT  TAT  GAC  ATG  AAG  CGG  GGC  TTT  GTG        251
Pro  Ala  Asn  Gly  Thr  Asp  Ile  Val  Tyr  Asp  Met  Lys  Arg  Gly  Phe  Val
               220                     225                    230

TAT  CTG  CAA  CCT  CAT  TCC  GAG  CAC  CAG  GGT  GTG  GTT  TAC  TGC  AGG  GCG        299
Tyr  Leu  Gln  Pro  His  Ser  Glu  His  Gln  Gly  Val  Val  Tyr  Cys  Arg  Ala
          235                          240                     245

GAG  GCC  GGG  GGC  AGA  TCT  CAG  ATC  TCC  GTC  AAG  TAC  CAG  CTG  CTC  TAC        347
Glu  Ala  Gly  Gly  Arg  Ser  Gln  Ile  Ser  Val  Lys  Tyr  Gln  Leu  Leu  Tyr
     250                          255                    260

GTG  GCG  G GTAAGCTGG  CCACCCTGC  CTAGATTCTA  GTTAGTCCCC  TGGTCAGTTT               404
Val  Ala  Val
265

CAGGTACTGC  TGTTCCCTG                                                                  423
```

( 2 ) INFORMATION FOR SEQ ID NO: 8:

( i ) SEQUENCE CHARACTERISTICS:
        ( A ) LENGTH: 239
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
        ( A ) NAME/KEY: exon 6
        ( B ) LOCATION: 46..185
        ( C ) IDENTIFICATION METHOD: experimental examination ( x i ) SEQUENCE DESCRIPTION: SEQ ID NO: 8:

```
TTACACTCGG  GGTACTCACT  CTGCCTGTTT  CGTGCTTGCT  TCCAG TT  CCC  AGT              53
                                                          Val  Pro  Ser

GGC  CCT  CCC  TCA  ACA  ACC  ATC  TTG  GCT  TCT  TCA  AAC  AAA  GTG  AAA  AGT       101
Gly  Pro  Pro  Ser  Thr  Thr  Ile  Leu  Ala  Ser  Ser  Asn  Lys  Val  Lys  Ser
270                      275                    280                    285

GGG  GAC  GAC  ATC  AGT  GTG  CTC  TGC  ACT  GTC  CTG  GGG  GAG  CCC  GAT  GTG       149
Gly  Asp  Asp  Ile  Ser  Val  Leu  Cys  Thr  Val  Leu  Gly  Glu  Pro  Asp  Val
                    290                    295                         300

GAG  GTG  GAG  TTC  ACC  TGG  ATC  TTC  CCA  GGG  CAG  AAG  GTAAGTGTTG                195
Glu  Val  Glu  Phe  Thr  Trp  Ile  Phe  Pro  Gly  Gln  Lys
               305                     310

TACCTGCATC  TCAGCCCCTG  CGTCTCAGCC  TCTGCATCTC  AGCC                                  239
```

( 2 ) INFORMATION FOR SEQ ID NO: 9:

( i ) SEQUENCE CHARACTERISTICS:
        ( A ) LENGTH: 551
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Homo sapiens ( v i i ) IMMEDIATE SOURCE:
        ( A ) LIBRARY: human DNA cosmid library ( i x ) FEATURE:
    ( A ) NAME/KEY: exon 7
    ( B ) LOCATION: 50..551
    ( C ) IDENTIFICATION METHOD: experimental examination ( x i ) SEQUENCE DESCRIPTION: SEQ ID NO: 9:

```
ATAGCAGCTT GTCCCTCTTG CTTCAGTCTT TGTGGGTGTC GTTAAACAG GAT GAA                    5
                                                          Asp Glu
                                                              315

AGG CCT GTG ACG ATC CAA GAC ACT TGG AGG TTG ATC CAC AGA GGA CTG                103
Arg Pro Val Thr Ile Gln Asp Thr Trp Arg Leu Ile His Arg Gly Leu
            320             325             330

GGA CAC ACC ACG AGA ATC TCC CAG AGT GTC ATT ACA GTG GAA GAC TTC                151
Gly His Thr Thr Arg Ile Ser Gln Ser Val Ile Thr Val Glu Asp Phe
            335             340             345

GAG ACG ATT GAT GCA GGA TAT TAC ATT TGC ACT GCT CAG AAT CTT CAA                199
Glu Thr Ile Asp Ala Gly Tyr Tyr Ile Cys Thr Ala Gln Asn Leu Gln
            350             355             360

GGA CAG ACC ACA GTA GCT ACC ACT GTT GAG TTT TCC TGACTTGGAA                     245
Gly Gln Thr Thr Val Ala Thr Thr Val Glu Phe Ser
            365             370             375

AAGGAAATGT AATGAACTTA TGGAAAGCCC ATTTGTGTAC ACAGTCAGCT TTGGGGTTCC              305

TTTTATTAGT GCTTGCCAG AGGCTGATGT CAAGCACCAC ACCCCAACCC CAGCGTCTCG               365

TGAGTCCGAC CCAGACATCC AAACTAAAAG GAAGTCATCC AGTCTATTCA CAGAAGTGTT              425

AACTTTTCTA ACAGAAAGCA TGATTTTGAT TGCTTACCTA CATACGTGTT CCTAGTTTTT              485

ATACATGTGT AAACAATTTT ATATAATCAA TCATTTCTAT TAAATGAGCA CGTTTTGTA               545

AAAAAT                                                                         551
```

( 2 ) INFORMATION FOR SEQ ID NO: 10:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 10:

```
ACCTTGTTCC TCCTGAAGAA AC                                                        22
```

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 11:

```
ACCGAGGGCC GAACGTTAGA                                                           20
```

( 2 ) INFORMATION FOR SEQ ID NO: 12:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 12:

ATTTCTCTCT CCTTACGTTT TGC                    23

( 2 ) INFORMATION FOR SEQ ID NO: 13:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 13:

TTACAAATCC TCAACCCTAC ACA                    23

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 14:

CCCAGCCAGG TCTGATTTGC                        20

( 2 ) INFORMATION FOR SEQ ID NO: 15:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 15:

GTTCCATTAA TGCACCAAGT ATTTT                  25

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 16:

AGCCTGTGCT CTTCCTTCCC                        20

( 2 ) INFORMATION FOR SEQ ID NO: 17:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 17:

GGGACTAACT AGAATCTAGG CA                     22

(2) INFORMATION FOR SEQ ID NO: 18:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: other nucleic acid (synthetic DNA)

(xi) SEQUENCE DESCRIPTION: SEQ ID NO: 18:

ACTCGGGGTA CTCACTCTGC 20

(2) INFORMATION FOR SEQ ID NO: 19:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: other nucleic acid (synthetic DNA)

(xi) SEQUENCE DESCRIPTION: SEQ ID NO: 19:

GGCTGAGATG CAGGTACAAC A 21

(2) INFORMATION FOR SEQ ID NO: 20:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: other nucleic acid (synthetic DNA)

(xi) SEQUENCE DESCRIPTION: SEQ ID NO: 20:

CTTCAGTCTT TGTGGGTGTC G 21

(2) INFORMATION FOR SEQ ID NO: 21:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: other nucleic acid (synthetic DNA)

(xi) SEQUENCE DESCRIPTION: SEQ ID NO: 21:

GTACACAAAT GGGCTTTCCA TAA 23